United States Patent [19]

McKenzie

[11] 4,212,392
[45] Jul. 15, 1980

[54] MEDICAL EMERGENCY TREATMENT KIT

[75] Inventor: Robert T. McKenzie, Manlius, N.Y.

[73] Assignee: Bristol-Myers Company, New York, N.Y.

[21] Appl. No.: 10,942

[22] Filed: Feb. 9, 1979

[51] Int. Cl.³ .............................................. B65D 69/00
[52] U.S. Cl. .................................... 206/571; 206/592; 292/251.5; 312/123; 312/126; 312/199; 312/270
[58] Field of Search ............... 312/117, 123, 125, 126, 312/, 199, 200, 249, 270, 214, 215; 206/570, 523, 524, 592, 571, 363, 365; 292/251.5

[56] References Cited

U.S. PATENT DOCUMENTS

| | | | |
|---|---|---|---|
| 1,405,311 | 1/1922 | Meyers | 312/199 |
| 1,526,507 | 2/1925 | Seward | 190/19 |
| 2,815,236 | 12/1957 | Lowinski | 292/251.5 |
| 3,181,693 | 5/1965 | Freistat | 206/523 |
| 3,844,597 | 10/1974 | Elrod et al. | 292/251.5 |

FOREIGN PATENT DOCUMENTS

| | | | |
|---|---|---|---|
| 847760 | 10/1939 | France | 312/199 |
| 1209747 | 3/1960 | France | 312/200 |

Primary Examiner—Herbert F. Ross
Attorney, Agent, or Firm—Roylance, Abrams, Berdo & Farley

[57] ABSTRACT

A portable medical kit is provided which maintains medicines, instruments and equipment secure when the kit is closed, presents all of the contained items in a readily visible and easily accessible manner when the kit is open, and provides unambiguous interrelation between specific medicines and instruments to aid the user. The kit can be wall-mounted, as when used in a hospital emergency room; is easily portable, and can be used free-standing on any suitable support surface.

8 Claims, 27 Drawing Figures

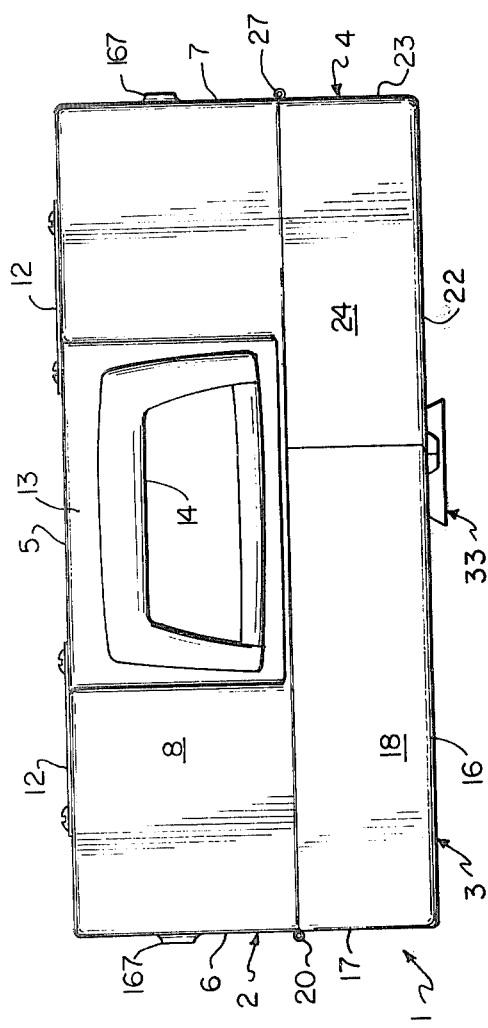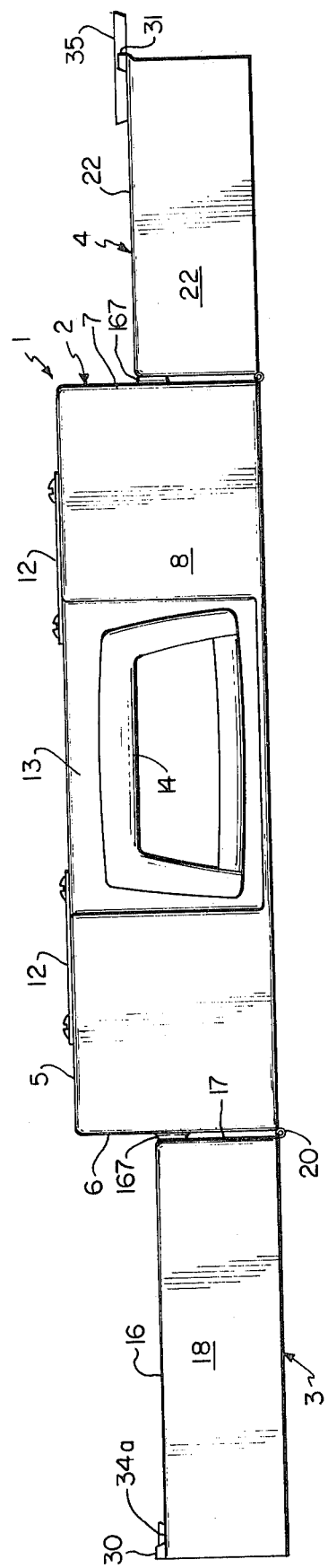

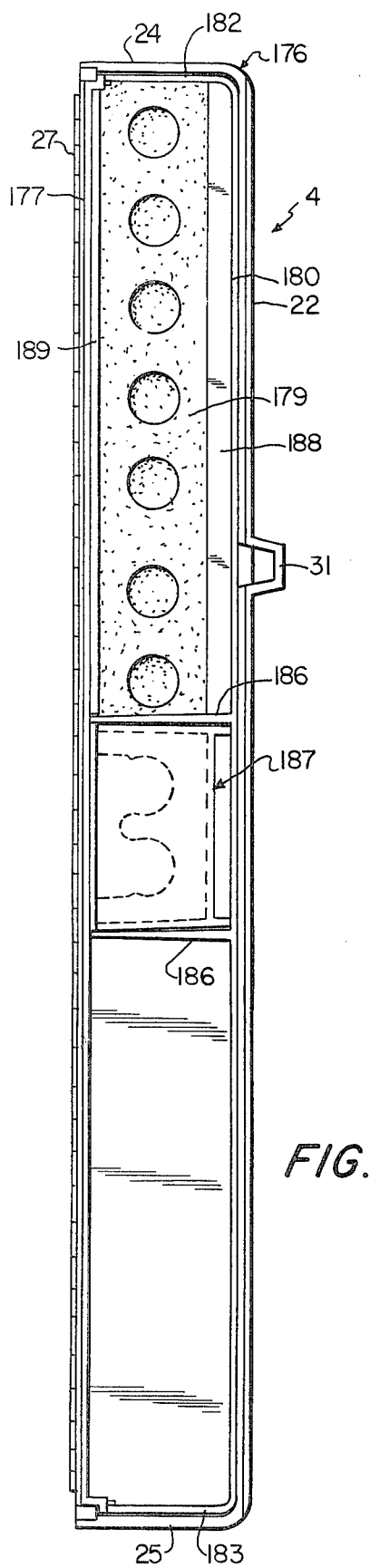
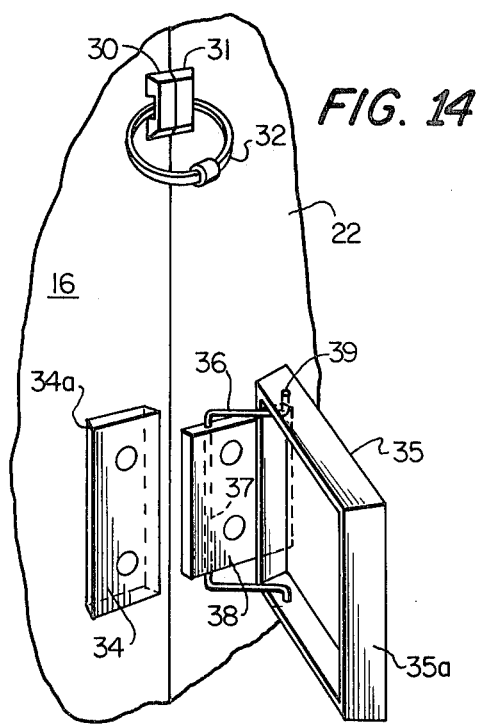
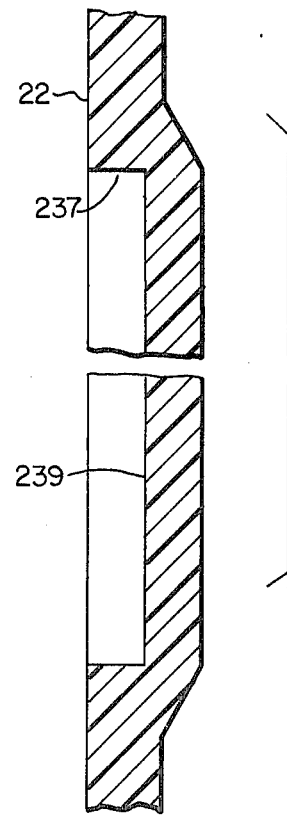
FIG. 13
FIG. 14
FIG. 15

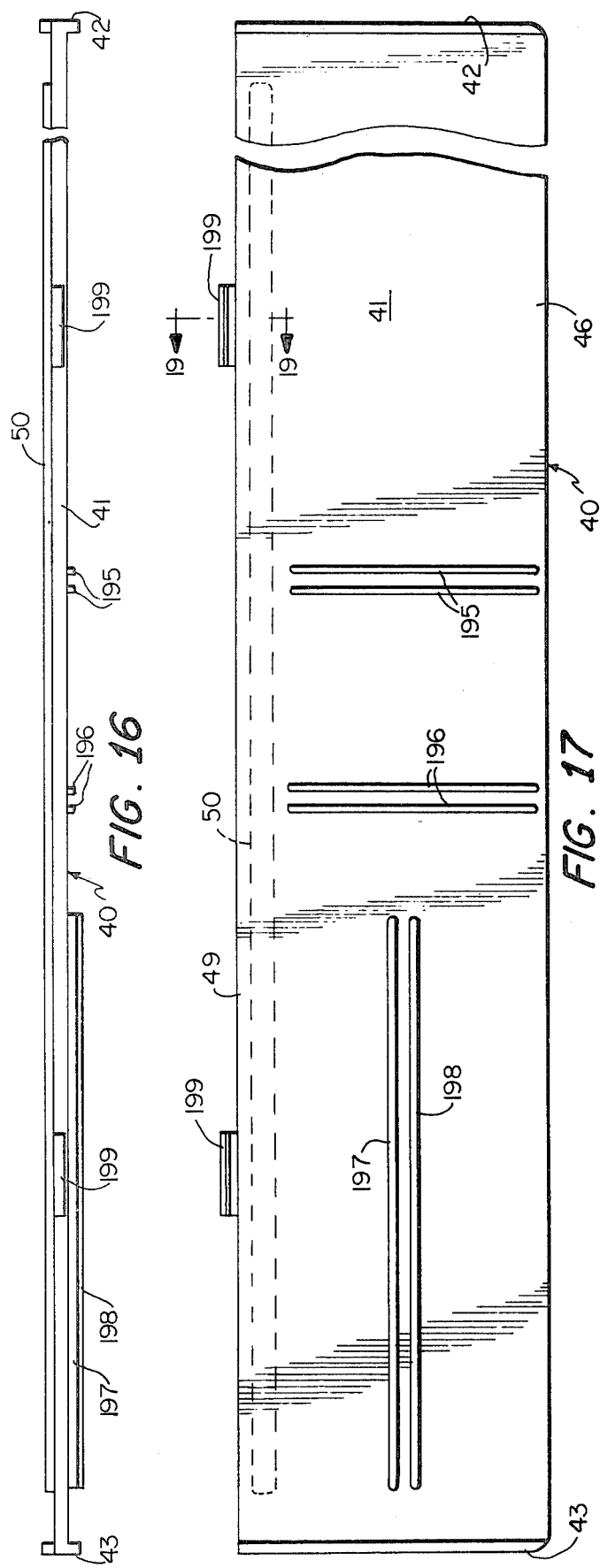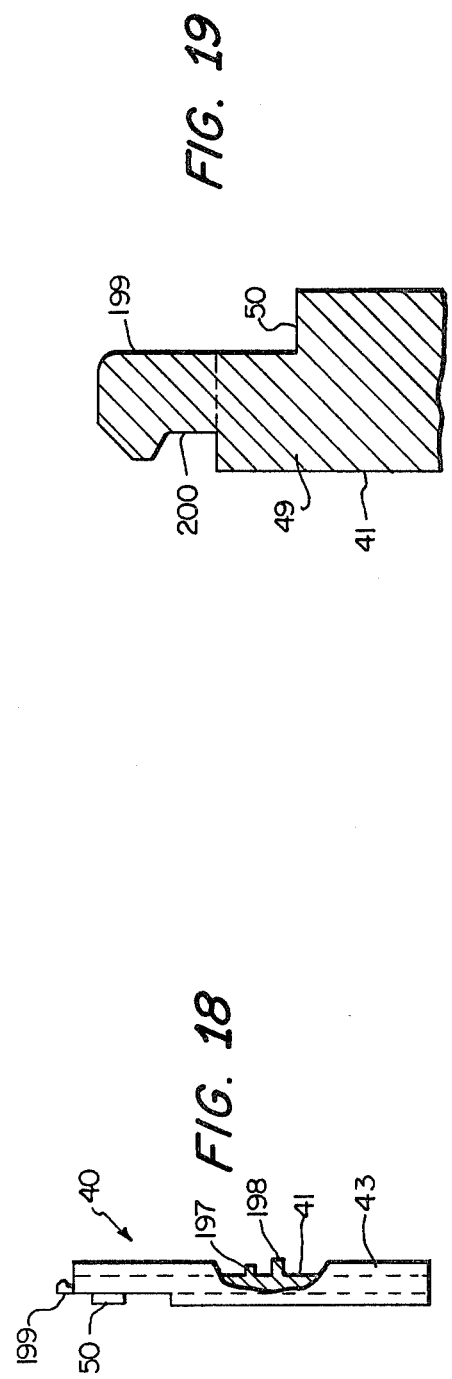

MEDICAL EMERGENCY TREATMENT KIT

RELATED APPLICATIONS

Ornamental design aspects related to the invention are disclosed and claimed in my copending design patent applications Ser. No. 931,836, filed Aug. 7, 1978, and Ser. No. 969,576, filed Dec. 14, 1978.

BACKGROUND OF THE INVENTION

Certain medical emergencies, of which cardiac failure and antiphylactic shock are examples, require that the patient be treated with the utmost alacrity and precision. Physicians and hospital personnel have developed remarkable skills in handling such emergencies, and the supporting drug and equipment industries have developed medicines, instruments and equipment which have greatly advanced the art of emergency medical treatment. Despite such advances, however, there has been a continuing need for an emergency kit which would with reliable certainty provide the physician or the paramedic with medicines, instruments and equipment necessary for emergency treatment, and would serve that purpose in locations, outside the usual hospital, where elaborate facilities are not available. In an effort to meet this demand, prior-art workers have provided so-called resuscitation carts, useful mainly in hospitals and hospital emergency rooms, but actual experience has shown that the usual resuscitation carts are poorly organized, excessively complex and, because of their complexity and size, are frequently not adequately serviced and cleaned so that, at the time of an emergency, the medicine or instrument needed may not actually be in the cart or may not be in usable condition. Because of the shortcomings of the usual resuscitation carts, it has recently been proposed to provide relatively smaller emergency kits which are intended to be replaced after use, as disclosed in "Cardiopulmonary Resuscitation Kits: A Simplified Approach", Robert L. Watson et al, *Military Medicine*, 141(6), pages 401–403 (June, 1976).

OBJECTS OF THE INVENTION

A general object of the invention is to devise a medical emergency treatment kit which will better serve to keep the necessary medicines, instruments and equipment secure during storage and transport and to present the same for quick, easy and certain selection during use of the kit in emergency treatment.

Another object is to provide such a kit which better lends itself to servicing to assure that the medicines are in place and not outdated.

A further object is to provide such a kit in which certain instruments, typically syringes, occupy specific positions correlated to the positions occupied by the medicine with which the instrument is to be used.

Yet another object is to provide such a kit which can be manufactured economically yet is adequately rugged to withstand transport and, when opened for use, is especially stable so as to be suited for use under emergency conditions.

SUMMARY OF THE INVENTION

Broadly considered, medical emergency treatment kits according to the invention comprise an upright main housing portion which defines a first storage space which opens forwardly; a secondary housing portion which defines a second storage space and is mounted on the first housing portion for movement between a closed position, in which the secondary housing portion covers at least a portion of the first storage space and the second storage space opens toward the first storage space, and an open position, in which the second storage space is disposed beside the first storage space and opens forwardly; first article-retaining means disposed in a predetermined location and orientation in the first storage space and comprising a plurality of retainers each occupying a different predetermined position on the first article-retaining means; and a second article-retaining means disposed in a predetermined location and orientation in the second storage space and comprising a plurality of retainers each occupying a predetermined location on the second article-retaining means, each of the predetermined locations on the second article-retaining means being aligned with at least one of the predetermined positions on the first article-retaining means so that when the secondary housing portion is in its open position the user of the kit, having chosen an article from the first article-retaining means, can quickly select a related article from the second article-retaining means without need for inspection of the related article to determine that it is correctly selected.

While more broadly applicable, the invention is especially useful in connection with cardiopulmonary resuscitation kits, with the articles in the first retaining means being containers of specific medicines and those in the second retaining means being syringes for administering the specific medicines.

IDENTIFICATION OF THE DRAWINGS

In order that the manner in which the foregoing and others objects are achieved according to the invention can be understood in detail, one particularly advantageous embodiment thereof will be described with reference to the accompanying drawings, which form part of the original disclosure of this application, and wherein:

FIG. 2 is a top plan view of the closed kit shown in FIG. 1;

FIG. 3 is a top plan view of the kit after the kit has been opened;

FIG. 13 is a side elevational view taken as indicated by line 13—13, FIG. 10;

FIG. 14 is a fragmentary perspective view illustrating a latch and a security band retainer employed to secure the kit in closed condition;

FIG. 15 is a fragmentary cross-sectional view taken generally on line 15—15, FIG. 1;

FIG. 16 is a front edge elevational view of a central vertical partition employed in the main portion of the housing of the kit;

FIG. 17 is a side elevational view of the partition of FIG. 16;

FIG. 18 is an end elevational view of the partition of FIG. 16, with a portion broken away for clarity of illustration;

FIG. 19 is an enlarged fragmentary cross-sectional view taken generally on line 19—19, FIG. 17;

DETAILED DESCRIPTION OF THE INVENTION

Figure 1:
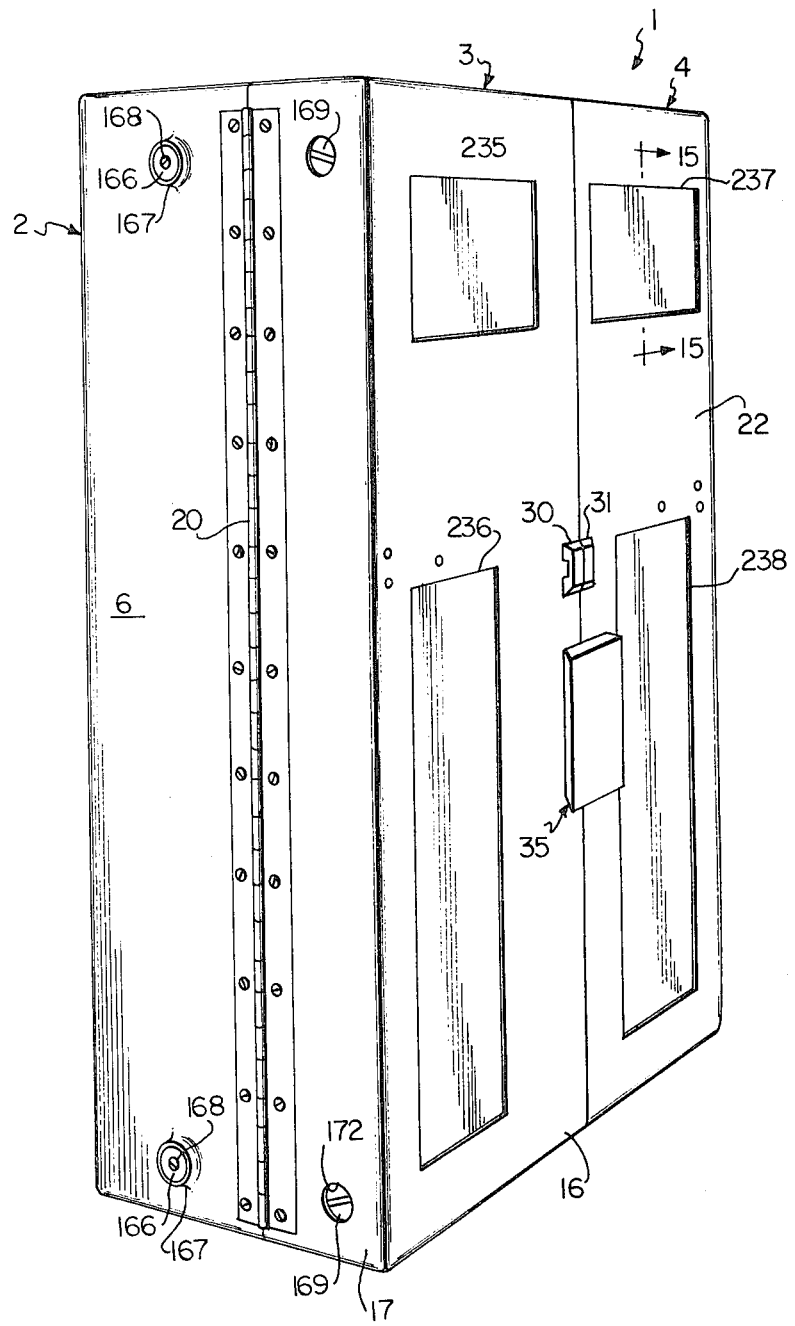
FIG. 1 is a frontal perspective view of a cardiopulmonary resuscitation kit according to the invention, showing the kit closed.

Referring first to FIGS. 1-5, the illustrated embodiment of the invention provides a cardiopulmonary resuscitation kit indicated generaly at 1 and comprising an upright main housing portion 2 and two secondary housing portions 3 and 4. Main housing portion 2 includes a flat rear wall 5, which is elongated rectangular in plan, two rectangular side walls 6, 7 joined to rear wall 5 along the respective side edges thereof, and two rectangular end walls 8, 9 joined to the rear wall along the top and bottom edges, respectively. Rear wall 5 is forwardly deformed, as at 10 and 11, FIG. 4, and two apertured hanger brackets 12 are secured to the outer surface of the wall so that the apertures of the brackets register with deformed areas 10, 11 and the kit can be supported by conventional hooks (not shown) on a wall or any other vertical structure. Upper end wall 8 is deformed to provide an upwardly opening recess 13 which accommodates a carrying handle 14 secured to wall 8. Bottom end wall 9 is flat and of such plan extent that the kit can be supported in stable standing fashion on a table, floor, vehicle seat or any flat horizontal surface. Walls 5-9 coact to define a first storage space 15 which opens forwardly.

Secondary housing portion 3 includes a generally flat main wall 16 of elongated rectangular plan form, a rectangular flat side wall 17 joined to one edge of wall 16, and two rectangular end walls 18 and 19 joined to the respective end edges of wall 16. The long dimension of the rectangle of wall 16 is equal to the long dimension of wall 5 of housing portion 2, but the short dimension of wall 16 is only slightly greater than half the short dimension of wall 5. As best seen in FIG. 1, an elongated hinge 20 has one of its plates secured to the flat frontal edge portion of side wall 6 and the other of its plates secured to the flat free edge portion of side wall 17 so as to mount housing portion 3 on housing portion 2 for pivotal movement between a closed position, seen in FIGS. 1 and 2, and an open position, seen in FIGS. 3 and 5. Walls 16-19 coact to define a second storage space 21 which opens toward space 15 when housing portion 3 is in its closed position, and which is located beside housing portion 2 and opens forwardly when housing portion 3 is in its fully open position. Since housing portion 3 has only one side wall, space 21 also opens away from wall 17.

Secondary housing portion 4 comprises a generally flat main wall 22 of elongated rectangular plan form, a rectangular flat side wall 23, and two rectangular end walls 24 and 25, walls 22-25 coacting to define a third storage space 26. An elongated hinge 27 has its plates secured respectively to the flat frontal edge portion of side wall 7 and the free edge portion of side wall 23. Housing portion 4 is thus mounted on housing portion 2 for pivotal movement between a closed position, FIGS. 1 and 2, and an open position, FIGS. 3 and 5. The long dimension of the rectangle of wall 22 equals that of wall 5, while the short dimension of the rectangle of wall 22 equals the difference between the width of wall 17 and the width of wall 5. Hence, when secondary housing portions 3 and 4 both occupy this closed positions, the secondary housing portions cooperate to fully close housing portion 2. Storage space 26 opens toward space 15 when housing portion 4 is in its closed position and is located beside housing portion 2 and opens forwardly when housing portion 4 is in its fully open position. Since housing portion 4 has only one side wall, storage space 26 also opens away from wall 23.

Figure 5:
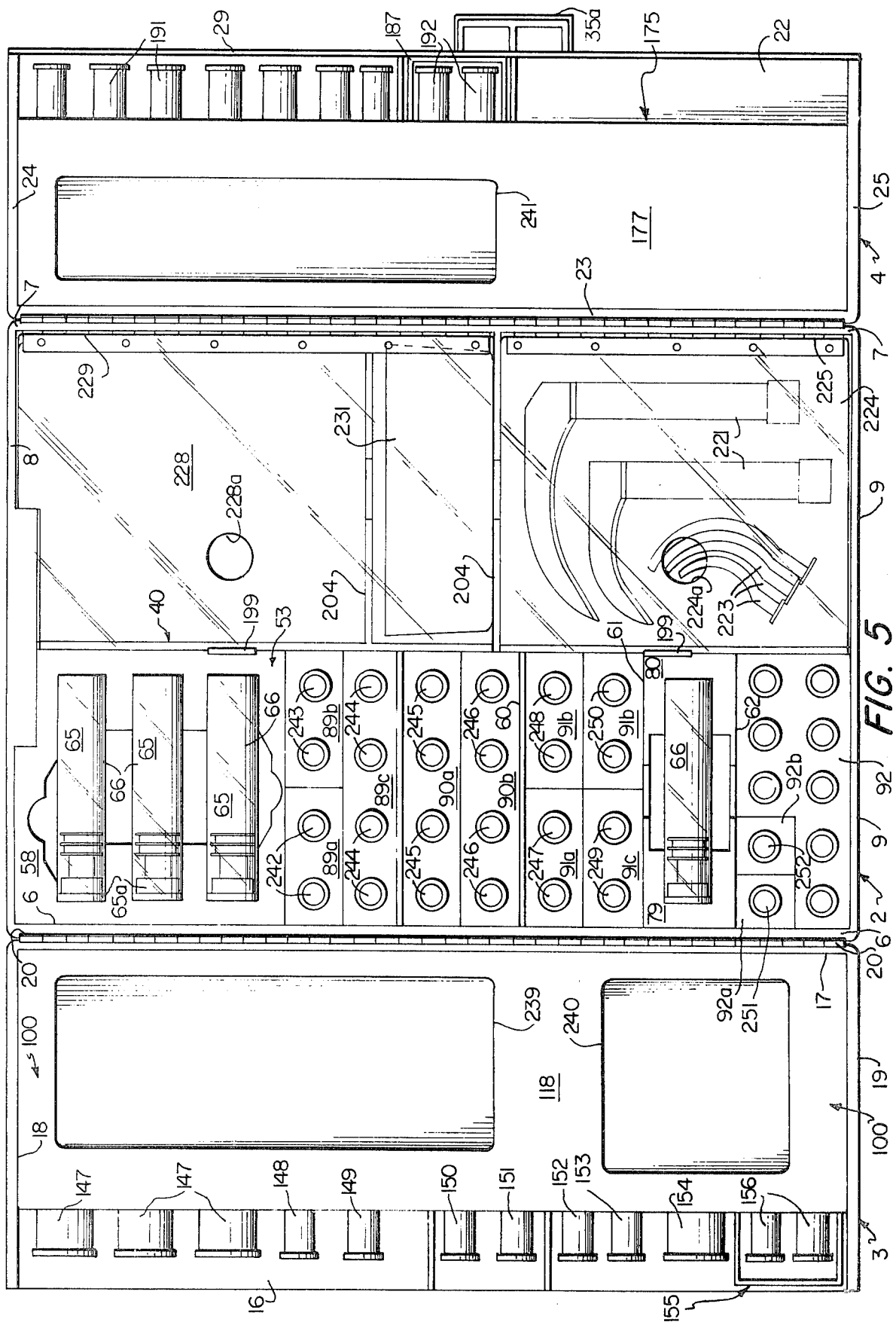
FIG. 5 is a front elevational view of the kit, when open as in FIG. 3, with typical contents shown in place.

As will be apparent from FIGS. 2 and 5, the free edges of the side walls and end walls of housing portions 3 and 4 mate with or abut the corresponding free edges of the respective side and end walls of housing portion 2 when portions 3 and 4 are swung to their closed positions. When the secondary housing portions are in their closed positions, the free edge of wall 16 mates with or abuts the free edge of wall 22, so that walls 16 and 22 then combine to form a complete front wall of kit 1. The free edge of wall 16 is advantageously externally notched, as at 28, FIG. 7, along its entire length, and the free edge of wall 22 internally notched along its entire length, as at 29, FIG. 11, so that a lip is provided on wall 22 to overlie the adjacent edge of wall 16 when portions 3 and 4 are closed. Adjacent its free edge, wall 16 is provided with an integral external protuberance 30, FIGS. 1, 7 and 13. Wall 2 is similarly provided with a protuberance 31, FIGS. 1, 11 and 14, so disposed as to mate with protuberance 30 when housing portions 3 and 4 are in their closed positions. Both protuberances have through passages, as at 31a, FIG. 11, so that a seal band 32, FIG. 14, can be passed through the aligned passages of the two protuberances, after the kit has been serviced and closed, and the kit cannot then be used without breaking the seal band to allow housing portions 3 and 4 to be moved to their open positions. Thus, presence of the seal band 32 properly in place can be used as reliable proof that the kit is in fact fully stocked and ready for use. A conventional latch 33 of the double pivot type is provided below the protubernaces 30, 31 to latch the secondary housing portions 3, 4 securely in their closed positions. As seen in FIGS. 3 and 13, latch 33 comprises a fixed catch member 34 rigidly mounted on wall 16 adjacent the free edge thereof, and a movable latch member 35 carried by wall 22. Member 35 is supported by a bail 36 journalled to move about a vertical pivot axis 37 in a member 38 fixed to wall 22, the ends 39 of the bail being journalled in the side walls of member 35 to provide a second pivot axis defined by bail ends 39. The latch is closed by swinging member 35 to bring slanted end wall 35a thereof into engagement behind the slanted edge 34a of member 34 and then pushing member 35 toward walls 16, 22. The latch is released by pulling the end of member 35 which is opposite wall 35a to swing that end of member 35 away from wall 22. When latched, member 35 remains in latched position because the pivotal axis at 39 is slightly nearer wall 22 than is the axis at 37.

Housing portions 2–4 are advantageously each in the form of an integral piece shaped from a thermoplastic polymeric material such as polycarbonate, acrylonitrilebutadiene-styrene copolymer, or high impact polystyrene.

Figure 8:
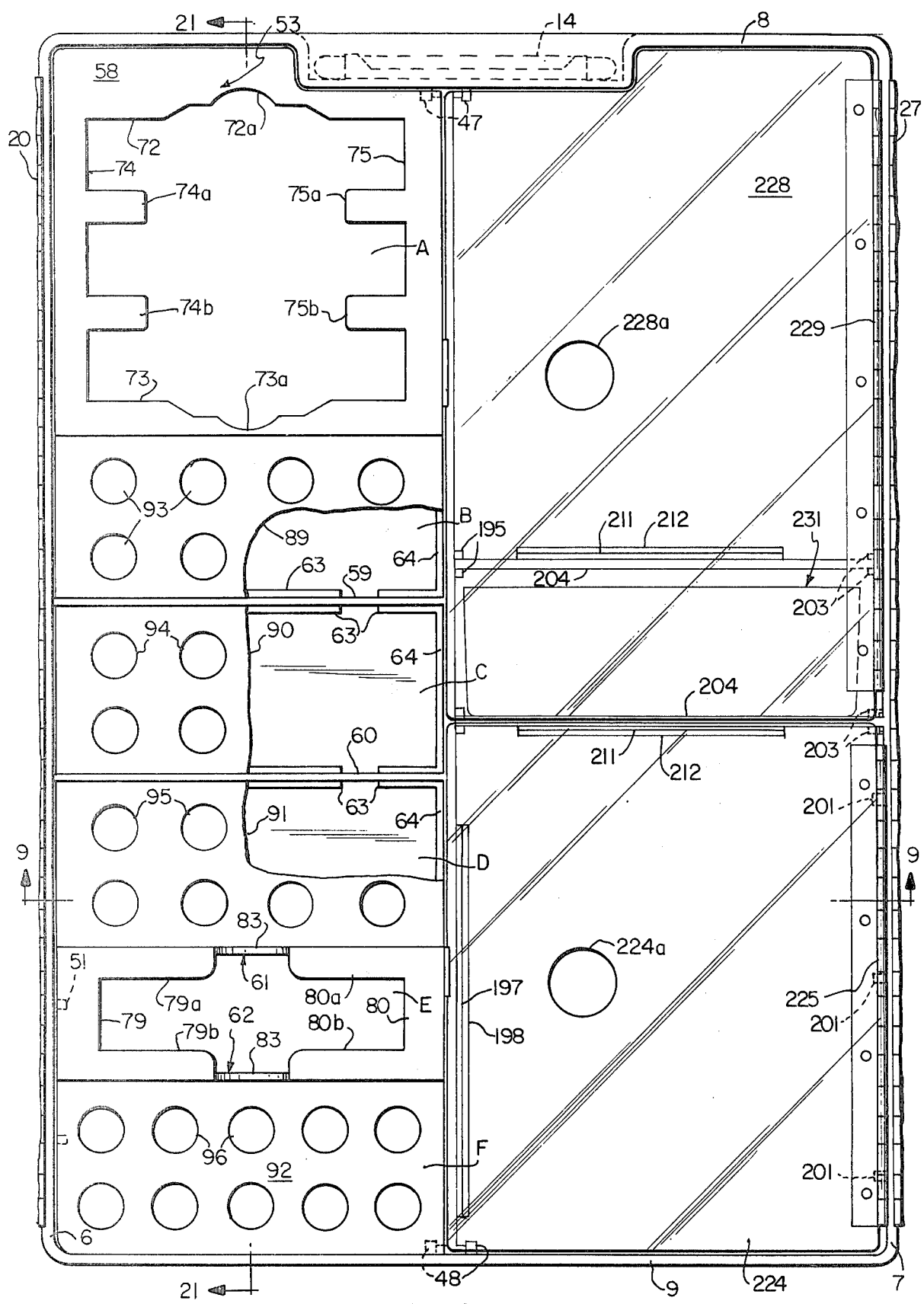
FIG. 8 is a front elevational view of the main portion of the housing of the kit, enlarged with respect to FIG. 5 and with contents removed and portions broken away for clarity of illustration.
Figure 9:
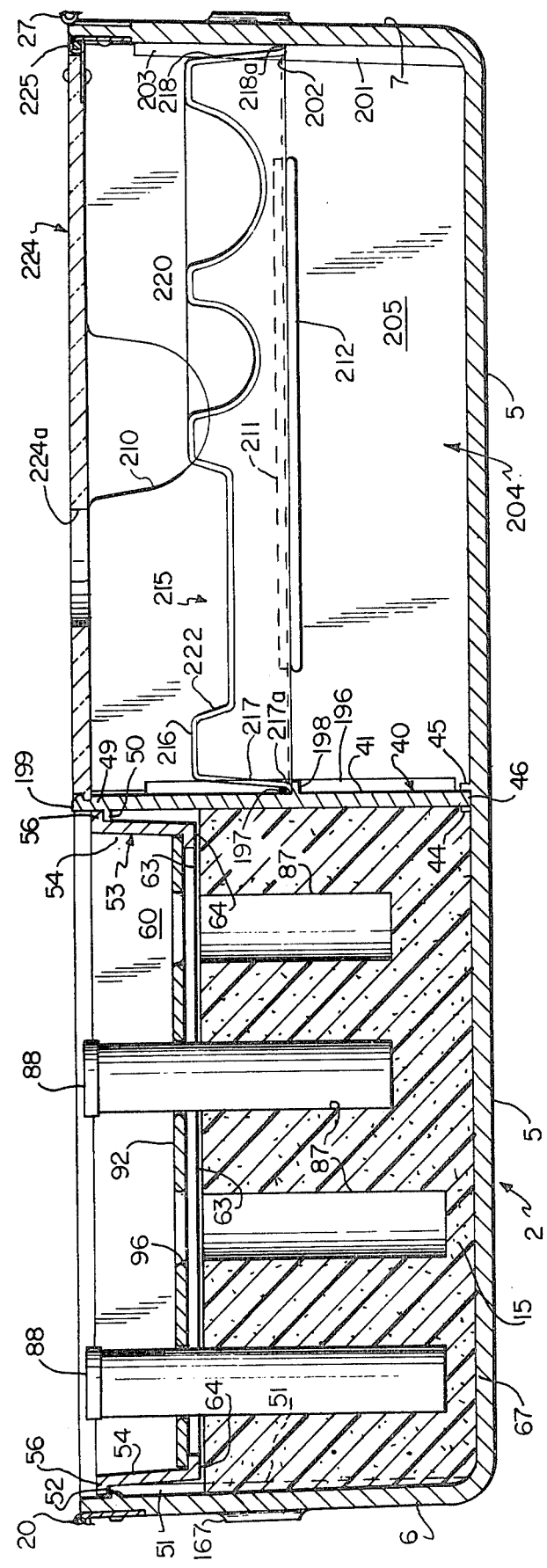
FIG. 9 is a transverse cross-sectional view taken generally on line 9—9, FIG. 8, and on a larger scale than FIG. 8.
Figure 10:
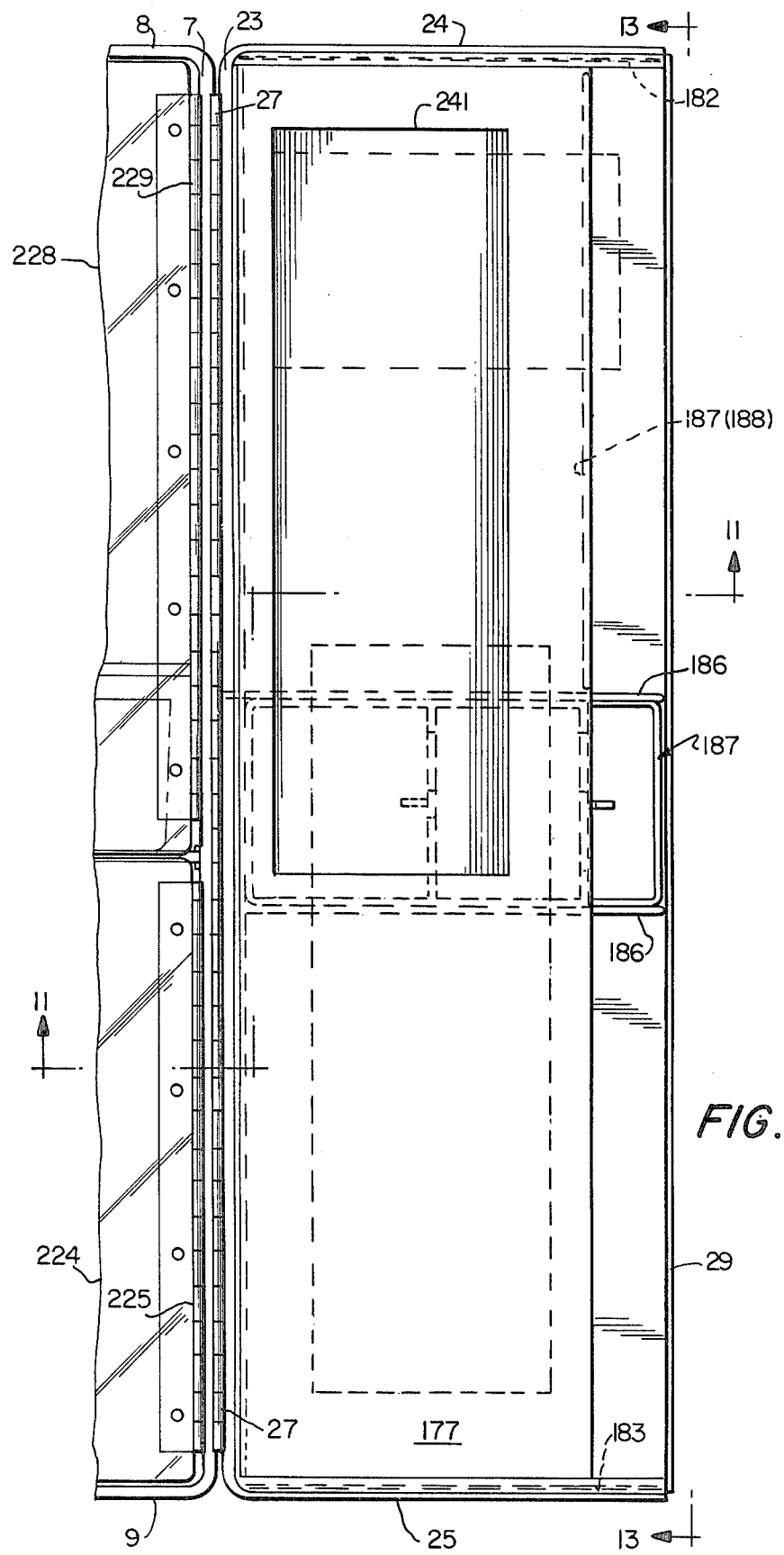
FIG. 10 is a front elevational view of another pivoted portion of the housing of the kit, enlarged with respect to FIG. 5 and with contents removed.

As seen in FIGS. 5, 8 and 9, storage space 15 is subdivided by a removable vertical partition 40, shown in detail in FIGS. 16–19. Partition 40 includes a flat main body 41 in the form of an elongated rectangle and having flanged ends 42 and 43 adapted to engage the inner surfaces of end walls 8 and 9, respectively, of housing portion 2, the length of the partition being such that the partition is engaged between end walls 8, 9 with a slight force fit. The position of the partition is fixed by two series of locator flanges 44 and 45, FIG. 9, on wall 5, between which the corresponding edge portion 46 of the partition is engaged, and two pairs of locator bases 47 and 48, FIG. 8, on end walls 8 and 9, respectively. One straight edge portion 49 of the partition lies generally in the open mouth of housing portion 2 and is provided with a straight ledge 50 which extends throughout most of the length of the partition and projects toward side wall 6 when the partition is properly installed. Along the portions of end walls 8, 9 extending between partition 40 and side wall 6, and along wall 6, a spaced series of support bosses 51, FIGS. 8 and 9, present end faces 52 lying essentially in the plane occupied by the outer surface of ledge 50 when partition 40 is properly installed. The combination of ledge 50 and bosses 51 serves to locate and support an article-retaining tray indicated generally at 53 and shown in detail in FIGS. 22 and 23.

Tray 53 is advantageously an integral substantially rigid piece shaped from thermoplastic material and, in plan, having a configuration matching that defined by the combination of partition 40, side wall 6, and the portions of end walls 8 and 9 which extend between the partition and side wall 6. Relatively shallow as compared to the depth of storage space 15, tray 53 has side walls 54 and end walls 55, all of which are rectangular in side elevation and slant inwardly at a small angle. Side walls 54 are formed at their front edges with outwardly projecting flanges 56 adapted respectively to engage ledge 50 and the faces 52 of bosses 51. The tray is divided by transverse partitions into six sections. A partition 57 cooperates with the adjacent end wall to define a first section A, FIG. 8, located near the top of the kit and having a front wall 58 but no rear wall. Partition 59 cooperates with partition 57 to define a second section B having either a front wall nor a rear wall. Partition 60 cooperates with partition 59 to define a third section C, and partition 61 with partition 60 to define a fourth section D, sections C and D being identical to section B. Partition 62 cooperates with partition 61 to define section E, which has a front wall but no rear wall. Partition 62 also cooperates with the adjacent end wall 56 of the tray to define section F, which is similar to sections B–D. Flanges 63 are provided along the rear edges of partitions 58–61 and flanges 64 are provided along the rear edges of side walls 54, in the areas occupied by sections B–D and F, all of flanges 63, 64 lying in a common plane parallel to that occupied by flanges 56.

In this embodiment, tray 53 constitutes part of article-retaining means employed to support injector vials containing measured doses of specific medicines. Thus, section A of the tray accommodates three larger cylindrical injector vials 65, a fourth larger cylindrical vial 66 is retained in part by section E, and sections B–D and F accommodate up to thirty-four smaller injector vials. The injector vials are constructed to cooperate with specific syringe units, for administering the medication, advantageously in accordance with U.S. Pat. Nos. 3,376,866, issued Apr. 9, 1968, and 3,378,008, issued Apr. 16, 1968, both to Robert W. Ogle. It is characteristic of such vials and syringe units that, once the proper vial and syringe unit has been selected, injection can be accomplished without requiring that the medicine be withdrawn from the vial into the syringe as a preparatory step.

Figure 22:
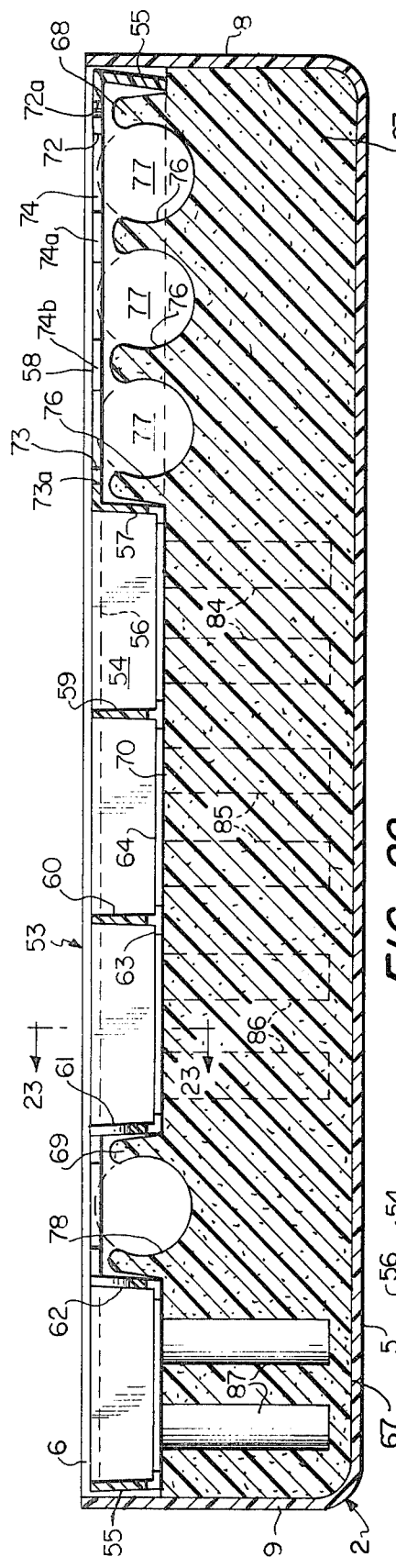
FIG. 22 is a vertical cross-sectional view taken generally on line 22—22, FIG. 8.
Figure 23:
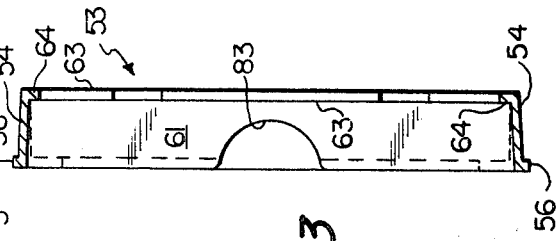
FIG. 23 is a fragmentary transverse cross-sectional view taken generally on line 23—23, FIG. 22.

Considering FIGS. 9 and 22, it will be seen that, when partition 40 and tray 53 are installed in housing portion 2, there is a substantial space between tray 53 and wall 5. That space is filled with suitable polymeric foam, advantageously foamed polyethylene. The space can be filled with a single pre-shaped body 67 of the foamed material, as shown, or with separate bodies of foam to coact each with one or more of the sections A–F of the tray. Body 67 is of such shape as to snugly engage walls 5, 6, 8 and 9 and partition 40. In the area of section A of tray 53, body 67 has a forwardly projecting portion 68 which substantially fills the space defined for section A by partition 57 and the cooperating portions of side walls 54 and adjacent end wall 55. Similarly, at tray section E, body 67 has a forwardly projecting portion 69 which substantially fills the space defined by partitions 61, 62 and the cooperating portions of side walls 54. In the areas coupled by tray sections B–D and F, body 67 has flat front faces 70 and 71, respectively, which lie in a plane immediately adjacent to the plane occupied by flanges 63, 64.

At tray section A, front wall 58 has a window defined by upper edge 27, FIG. 8, lower edge 73 and side edges 74 and 75. Upper edge 72 is upwardly offset at 72a and lower edge 73 is downwardly offset at 73a. Side edges 74 and 75 are interrupted by projections 74a, 74b and 75a, 75b, respectively, projections 74a and 75a being aligned transversely across the window and extending toward each other, and projections 74b and 75b being similarly arranged. As best seen in FIG. 22, portion 68 of foam body 67 has three identical transversely extending recesses 76 of circular transverse cross section, the circular side wall of each recess 76 extending for approximately 180°. The diameter of recesses 76 approximates that of vials 65. Portion 68 of foam body 67 is substantially wider than vials 65 are long, and recesses 76 have flat end walls 77 spaced apart by a distance slightly smaller than the length of vials 65. The foamed polymeric material of body 67 is capable of limited resilient deformation and of returning to its normal undeformed state when released. When a vial 65 is pushed firmly into one of the recesses 76, the vial is held in compression between the end walls 77 of the recess and is thus retained in the recess. The uppermost recess 76 is centered on the space between projections 74a, 75a, on the one hand, and edge 72, on the other. Similarly, the next lower recess 76 is centered on the space between the two sets of projections 74a,b and 75a,b. The lower one of the three recesses 76 is centered between projections 74b, 75b, on the one hand, and edge 73, on the other. While the material and dimensions of tray 53 are such that the tray is self-supporting, wall 58 is somewhat flexible and the spaces between projection 74a and edge 72, and between projections 74a and 74b, and between projection 74b and edge 73 are slightly less than the diameter of vials 65 so that window edge portions of wall 58 overlap the vials slightly. Such overlap aids in retention of the vials, but flexibility of wall 58 allows the wall to deform and release the vials under the force of manual withdrawal. Offset portion 72a of window edge 72 allows entry of a finger to allow the user to grasp the uppermost vial 65.

Portion 69 of foam body 67 is similarly provided with a single recess 78, identical to recesses 76, to accommodate vial 66 in tray section E. The front wall for section E comprises two complementary portions 79 and 80, FIG. 8, which cooperate to form a window defined by upper portions 79a and 80a, side edges 81 and 82, and lower portions 79b and 80b. Recess 78 and front wall portions 79a, 79b, 80a and 80b are dimensionally related to the vial as earlier described with reference to recesses 76. As seen in FIG. 22, partitions 61 and 62 are provided with access notches 83 to allow the user to grasp vial 66.

At tray section B, foam body 67 is provided with eight identical cylindrical bores 84, FIG. 22, arranged in two sets of four bores spaced apart transversely of the body, the two sets being spaced apart vertically, and the bores opening forwardly through front face 70. Body 67 is similarly provided with eight bores 85 in the location of tray section C and eight bores 86 in the location of tray section D. In the area of tray section F, body 67 is provided with ten cylindrical bores 87 arranged in two horizontally spaced sets of five each. All of bores 85–87 are identical to bores 84. Each of bores 84–87 is dimensioned to receive and snugly embrace an injector vial 88 in the fashion seen in FIG. 9, injector vials 88 being of the same type as but of smaller diameter than vials 65, 66.

As seen in FIG. 8, tray 53 accommodates a flat rectangular plate 89 in section B, identical plates 90 and 91 in sections C and D, and a similar plate 92 in section F, each plate 89–92 being engaged with the corresponding flanges 63, 64 and restrained by the adjacent partitions and side wall portions of the tray, in the fashion seen in FIG. 9. Plate 89 has eight circular openings 93 arranged in two series of four each with each opening 93 being located to register with a different one of the eight bores 84 in foam body 67. Plates 90 and 91 are similarly provided with openings 94 and 95, respectively, with each opening 94 disposed to register with a different one of bores 85 and openings 95 each disposed to register with a different one of bores 86. Plate 92 is provided with ten circular openings 96 disposed to register each with a different one of bores 87 in body 67. All of openings 93–96 are dimensioned to lightly embrace an injector vial 88 in such fashion that the plates assist in locating and retaining the vials but the vials can be easily inserted and withdrawn through the openings in the plates. In addition to serving to locate and support vials 88, plates 89-92 provide selectively colored areas by which the medicines in the various vials can be identified, as later described.

An article-retaining unit 100, FIGS. 5–7 and 12, is removably retained in the second storage space 15. Unit 100 comprises an outer shell, indicated generally at 101, a cover 102, a larger body 103, FIG. 7, of foamed polymeric material, and a smaller body 104, FIGS. 7 and 12, of foamed polymeric material. Shell 101 is adapted to nest in secondary housing portion 3 with a snug fit. Advantageously molded as a single piece from suitable polymeric material such as acrylonitrile-butadiene-styrene copolymer, shell 101 comprises a main wall 105 having the same plan configuration as housing wall 16, a side wall 106, an upper end wall 107 and a lower end wall 108. Though shell 101 is dimensioned and shaped to be snugly received in space 15, end walls 107 and 108 of the shell slidably engage end walls 18 and 19, respectively, of housing portion 3 so that unit 100 can be pushed into space 15. In a location near side wall 17, housing wall 16 is provided with a rectangular notch 109, FIG. 7. Wall 105 of unit 100 has a U-shaped cutout defining a catch 110 so located and dimensioned, as shown, as to engage one edge of notch 109 and restrain unit 100 against movement away from wall 17. Main wall 105 and end walls 107, 108 of shell 101 stop slightly short of the free edge of wall 16 when the shell is in its fully nested position, so that the free side edge 111, FIG. 7, of wall 105 is adjacent and parallel to the free edge of wall 16. A straight retaining flange 112 is formed integrally with wall 105 and extends parallel to edge 111 in a location spaced from edge 111 toward side wall 106. Opposite wall 105, end walls 107 and 108 have edges 113 and 114, respectively, which lie in a plane parallel to wall 105. Side wall 106 has a free edge 115 parallel to wall 105 and spaced slightly further from wall 105 than are edges 113, 114. Two stiffening partitions 116 are formed integrally with wall 105, are spaced apart vertically, and extend horizontally, being limited to the space between edge 111 and flange 112 in an area near the midpoint between end walls 107, 108. Nearer lower end wall 108, wall 105 has an integrally formed partition 117 which extends parallel to wall 108 for the full distance between edge 111 and side wall 106. Retaining flange 112 stops at partition 117, so that the space between partition 117 and end wall 108 is completely open.

Figure 7:
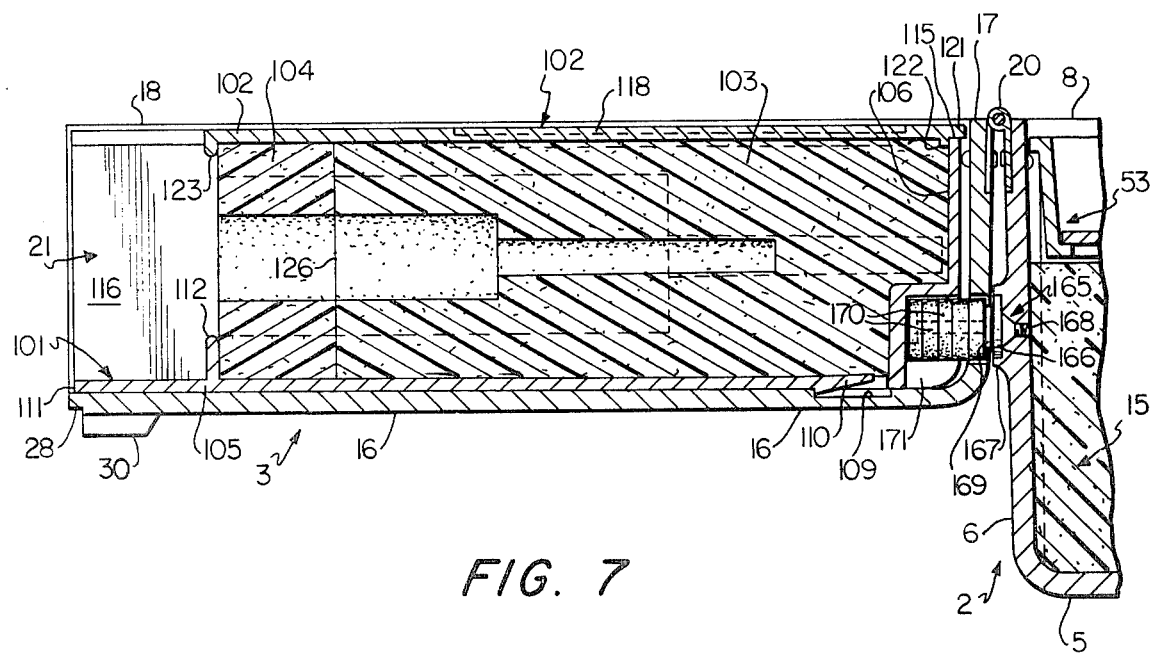
FIG. 7 is a transverse cross-sectional view taken generally on line 7—7, FIG. 6.
Figure 12:
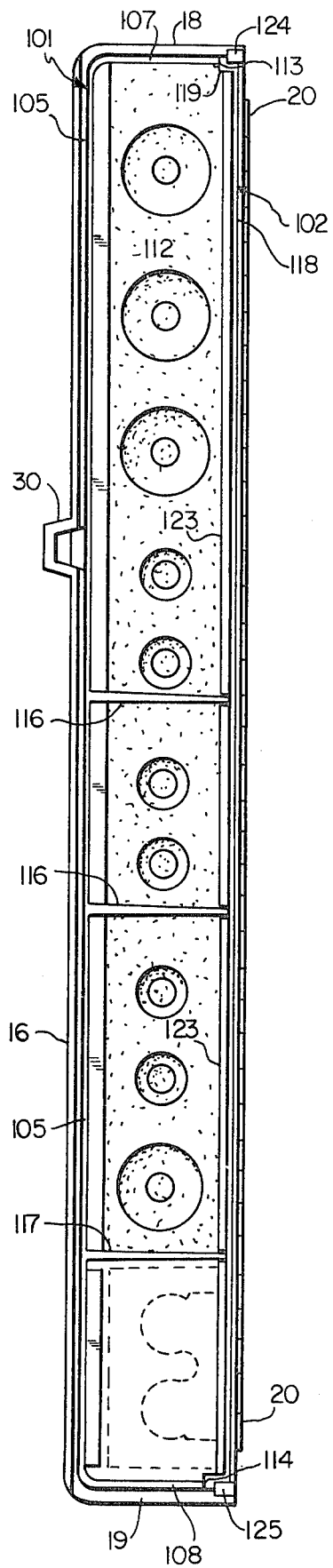
FIG. 12 is a side elevational view taken as indicated by line 12—12, FIG. 6.
Figure 4:
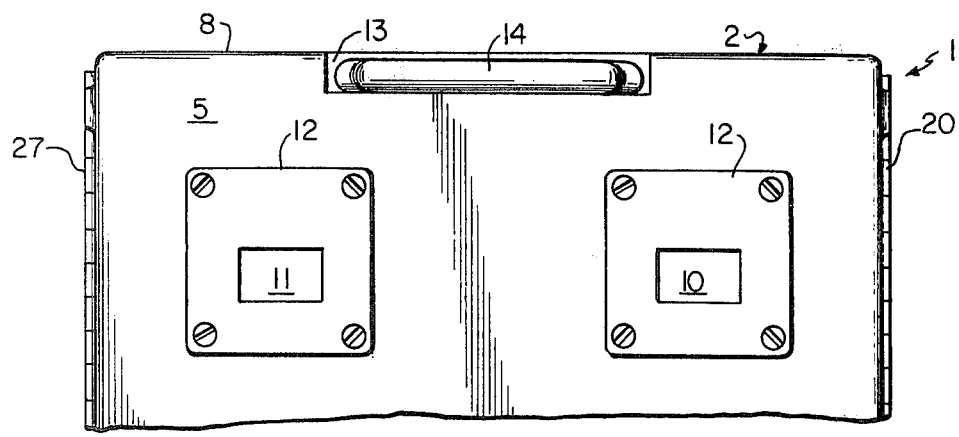
FIG. 4 is a fragmentary rear elevational view of the closed kit.
Figure 20:
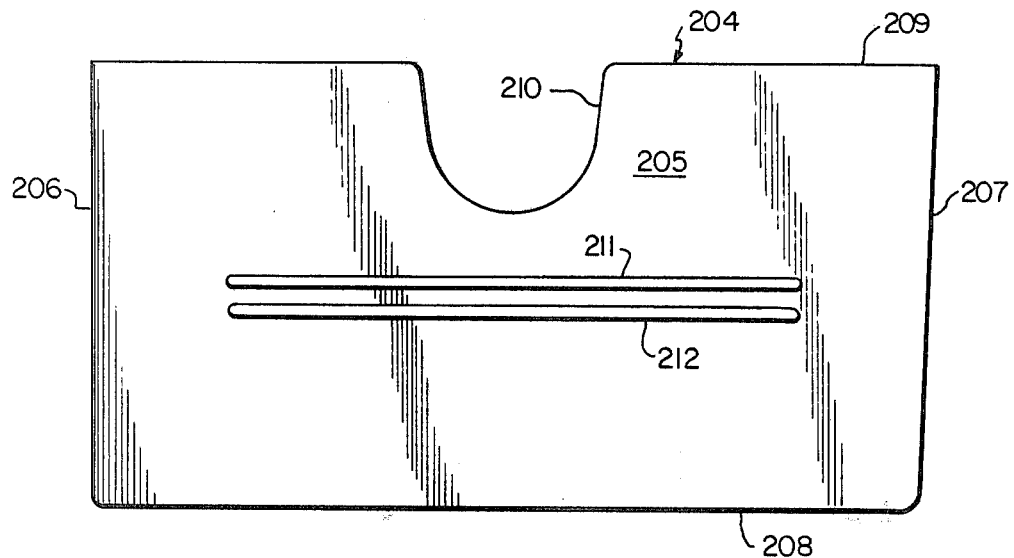
FIG. 20 is a plan elevational view of a horizontal partition employed in the main housing portion of the kit.
Figure 21:
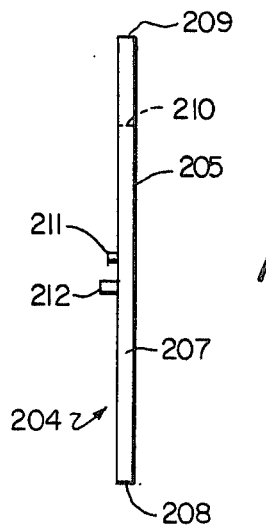
FIG. 21 is an end elevational view of the partition of FIG. 20.

Cover 102 is also made as an integral piece from suitable polymeric material, such as acrylonitrile-butadiene-styrene copolymer, and includes a flat main body 118 of plan shape and dimensions to fill that portion of the generally rectangular space defined by the free edges of side wall 106, and end walls 107, 108 which lies between wall 106 and flange 112. As best seen in FIG. 12, cover body 118 has an offset straight edge portion 119 dimensioned to seat against free edge 113 of end wall 107 of the shell, and an offset straight edge portion 120 dimensioned to seat against free edge 114 of end wall 108. With portions 119, 120 so seated, side edge portion 121 of body 118 extends over and seats on free edge 115 of side wall 106. A straight locator rib 122, FIG. 7, is provided on body 118 adjacent and parallel to edge portion 121 to engage the inner face of shell side wall 106. At its edge opposite portion 121, body 118 has a straight inturned retaining flange 123 which is coplanar with flange 112 when the cover is properly fitted to shell 101 and which is appropriately notched to accommodate partitions 116 and 117 so that body 118 can directly engage the partitions. Considering FIG. 12, it will be seen that the free edge of end wall 18 of housing portion 3 is provided with a longitudinal notch which cooperates with offset edge portion 119 of the cover to provide a straight recess of square transverse cross section into which a square retaining strip 124 is forced to secure that end of the cover. The free edge of end wall 19 is similarly notched to accommodate retaining strip 125.

Before cover 102 is applied to shell 101, foam bodies 103 and 104 are placed in the shell. Body 103 can, for example, be of closed cell polystyrene foam of relatively higher compressive strength, and body 104 can, for example, be of closed cell low density polyethylene foam of lower compressive strength but higher resiliency. Body 103 is shaped and dimensioned to fill all of the space between wall 105 and cover body 118 from partition 117 to end wall 107 except for the space adjacent retaining flanges 112, 123 except that the flat side face 126 of body 103 is spaced from and directed toward those flanges. Body 104 is of rectangular transverse cross section and completely fills the space between face 126 of body 103 and retaining flanges 112, 123. Body 103 is provided with three larger bores 127-129, FIG. 6, six smaller bores 130-135, and a larger bore 136. Bores 127-136 are each adapted to receive a syringe of specific size and therefore each includes a portion of larger diameter, as at 135a, FIG. 7, to accommodate the syringe barrel, and a portion of smaller diameter, as at 135b, to accommodate the needle housing of the syringe. Bores 127-136 extend horizontally from face 126 toward side wall 106, with the larger portions opening through face 126 and the smaller portions stopping short of wall 106.

Body 104 is provided with a plurality of through bores 137-146 each coaxially aligned with a different one of bores 127-136, respectively, each bore 137-146 having a diameter approximately equal to that of the larger diameter portion of the one of bores 127-136 with which it is aligned. Advantageously, the diameter of each bore 137-146 is slightly smaller than the outer diameter of the barrel of the syringe to be accommodated in the bore, so that the syringe will be held in hoop compression by the foam material of body 104.

Recognizing that hinge 20 maintains housing portion 3 in stable vertical position relative to main housing portion 2, larger bores 127-129 are aligned horizontally each with a different one of the recesses 76 and, therefore, each with a different one of the three larger injector vials 65 retained in space 15 by the combination of tray 53 and foam body 67. Three larger syringes 147, FIG. 5, are inserted each in a different one of bores 127-129, these syringes being of proper size to accept the larger vials 65. Similarly, bore 130 is aligned horizontally with the four smaller injector vials 88 retained in the upper four bores 84 in body 67 in tray area B, and a smaller syring 148, FIG. 5, is inserted through bore 140 into bore 130 so as to be horizontally aligned with those four injector vials 88, syringe 148 being sized to accept any vial 88. Bore 131 is aligned horizontally with the lower four bores 84 and a syringe 149 identical to syringe 148 is accommodated by bore 131. Bores 132, 133 are likewise each aligned with a different one of the two sets of bores 85 for tray area C, and since smaller vials 88 are disposed in bores 85, syringes 150 and 151, identical to syringe 148, are provided in bores 132 and 133, respectively. In similar fashion, bores 134, 135 are each aligned horizontally with a different one of the two sets of bores 86 for tray area D, and syringes 152 and 153, identical to syringe 148, are provided in bores 134 and 135, respectively. Bore 146 is aligned horizontally with the recess 78 provided in body 67 at tray area E, and since recess 78 retains a larger injector vial 66, a larger syringe 154 sized to accept vial 66 is provided in bore 146.

Figure 6:
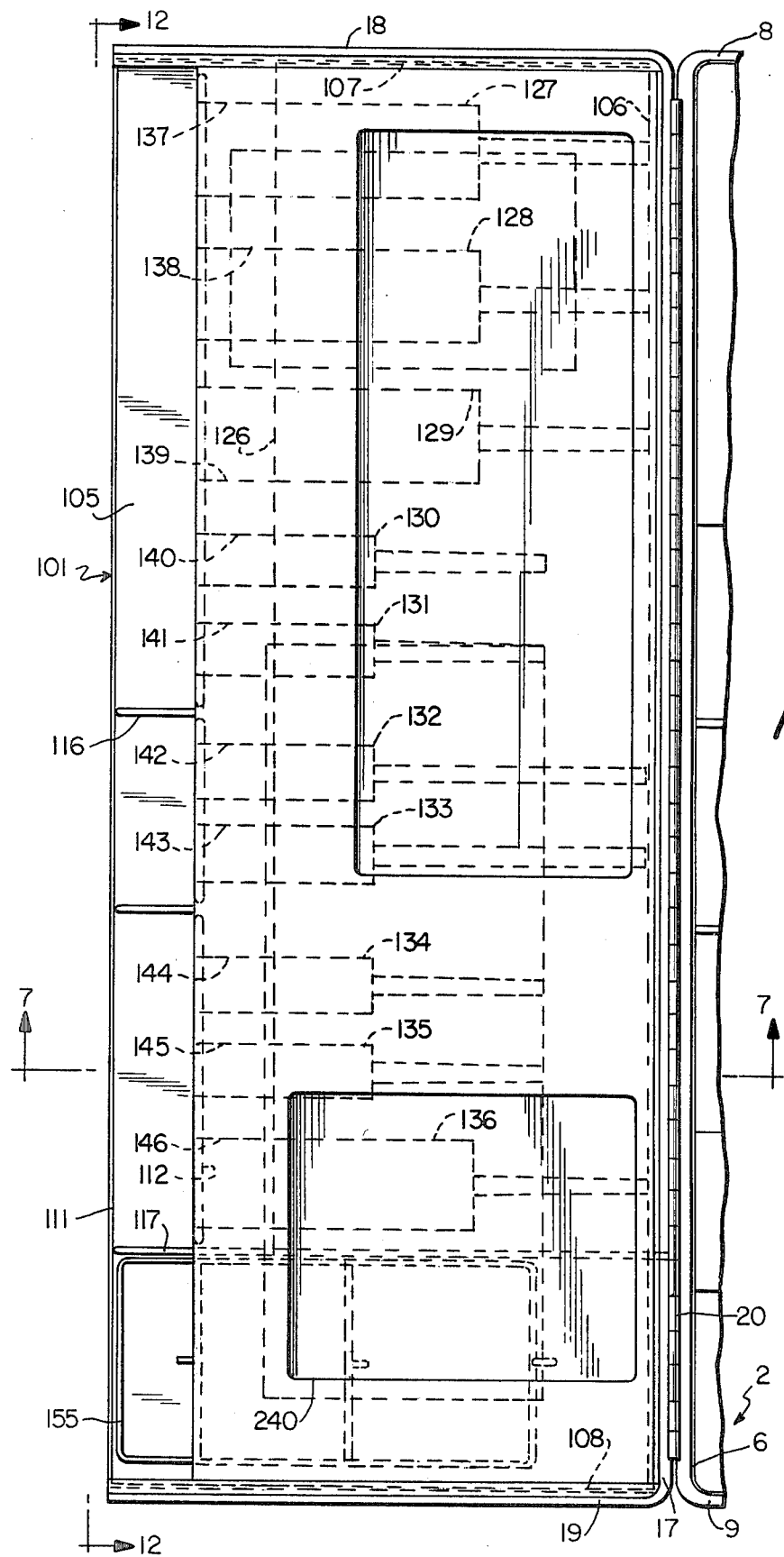
FIG. 6 is a front elevational view of one pivoted housing portion of the kit, enlarged with respect to FIG. 5 and with contents removed.
Figure 24:
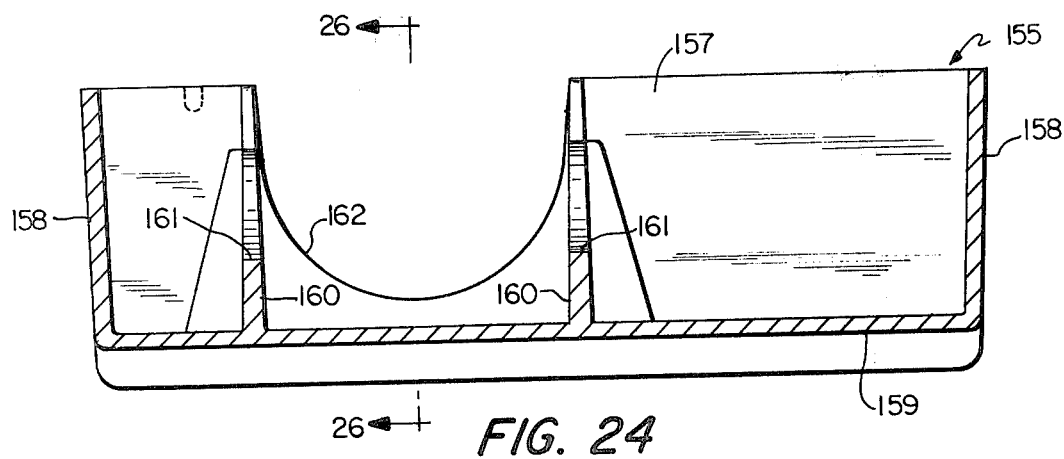
FIG. 24 is a cross-sectional view, taken generally on line 24—24, FIG. 25, of an article-retaining tray employed in one pivoted housing portion of the kit.
Figure 25:
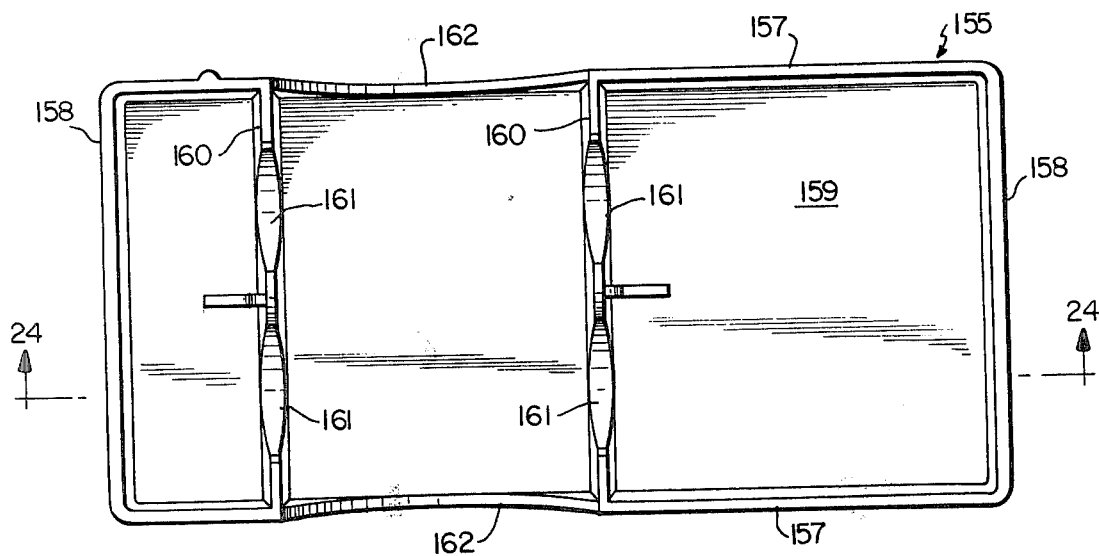
FIG. 25 is a top plan view of the tray of FIG. 24.
Figure 26:
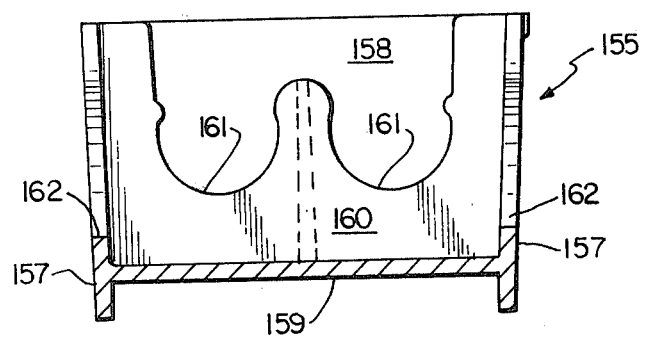
FIG. 26 is a transverse cross-sectional view taken generally on line 25—25, FIG. 23.

The space in unit 100 between partition 117 and end wall 108 accommodates a tray 155, FIGS. 24-26 adapted to retain two syringes 156, FIG. 5, which, because larger at the point than at the plunger end, cannot be inserted into bores in the manner described above. Tray 155 has flat side walls 157, end walls 158 and a flat rectangular bottom wall 159 which coact to define a space across which two transverse partitions 160 extend. Each partition has two notches 161 each extending circularly for slightly more than 180° and opening toward the open top of the tray, the notches being aligned lengthwise of the tray so that each aligned pair of notches will accept and retain one of the syringes 156. Side walls 157 are cut away arcuately at 162 between partitions 160 for finger access. As seen in FIGS. 5 and 6, the length of tray 155 is slightly less than the distance between edge 111 and side wall 106 but greater than the space between retaining flange 123 and side wall 106 so that, when the tray is fully nested in the space between partition 117 and end wall 108, an end portion of the tray and the corresponding ends of the syringes 156 retained by notches 161 are exposed to view.

As will be clear by comparison of FIGS. 6 and 7 with FIG. 5, body 118 of cover 102 covers only that portion of wall 105 which is occupied by foam bodies 103, 104 and the area on the side of flanges 112, 123 opposite the foam bodies is unobstructed, so that the ends of all of the syringes 147-156 are exposed to view.

When housing portion 3 has been swung to the fully open position, FIG. 7, side wall 17 is immediately adjacent the outer face of side wall 6 of the main housing portion, and cover 102 is then substantially coplanar with support flanges 56 of tray 53. To maintain housing portion 3 stably in its fully open position under conditions of use encountered, for example, in a moving vehicle, two magnetic latches, one of which is shown at 165 in FIG. 7, are provided. Each latch comprises a flat magnetic disc 166 disposed in a conforming recess in a boss 167 formed integrally with side wall 6 of housing portion 3 and secured rigidly to wall 6 as by a countersunk screw 168. Each latch also comprises a circular flat magnet 169 carried by a support comprising a plurality of circular resilient washers 170 which are held as a stacked series by a screw (not shown) in such fashion that the screw can be manipulated to apply axial compression to the washers. Walls 105 and 106 of shell 101 are deformed to provide a cavity 171, FIG. 7, in which the washers are disposed. Side wall 17 of housing portion 3 is provided with a circular opening 172 through which the assembly of supporting washers 170 and magnet 169 extends. With the assembly of washers disposed in cavity 171 as shown, placing of the resilient washers under axial compression by manipulation of the screw causes the washers to expand radially into tight retaining engagement with the walls of the cavity. The effective length of the assembly of washers, when so compressed, is such that, when housing portion 3 is in its fully open position, the magnet 169 of each latch 165 engages its cooperating magnetic disc 166. As seen in FIG. 1, latches 165 are located respectively near the top and bottom of the housing.

Secondary housing portion 4 is equipped with a third article-retaining unit 175, FIGS. 5, 10, 11 and 13, which is generally similar to unit 100. Thus, unit 175 comprises a shell 176 and a cover 177 which combine to enclose larger foam body 178 and smaller foam body 179, FIG. 11. Shell 176 has main wall 180, side wall 181 and end walls 182, 183 and is of such shape and size as to be snugly received in third storage space 26 with the walls of shell 176 directly engaging the respective walls of housing portion 4. Wall 22 is provided with a notch 184 and wall 180 with a catch 185, FIG. 11, to restrain the shell, once in place, against movement away from side wall 23. Midway of its vertical length, shell 176 includes two integrally formed horizontal partitions 186 spaced apart to slidably accommodate a syringe tray 187, FIG. 13, identical to tray 155. Wall 180 carries an integrally formed retaining flange 188 which extends throughout the space between end wall 182 and the upper one of partitions 186. Cover 177 has a retaining flange 189 aligned with flange 188, the two flanges projecting toward each other in the assembled device. Foam bodies 178, 179 extend for the full distance between end wall 182 and the upper partition 186 and combine to completely fill the space between flange 188 and side wall 181. Foam bodies 178, 179 are provided with bores 190, FIGS. 11 and 13, to accommodate and retain spare syringes 191, FIG. 5, in the same manner described with reference to unit 100. Tray 187 carries extra syringes 192, FIG. 5, in the same manner that tray 155 retains syringes 156. The space between lower partition 186 and end wall 183 opens only away from side wall 181 and is dimensioned to retain, e.g., a sphygmomanometer and a small stethoscope (not shown).

Figure 11:
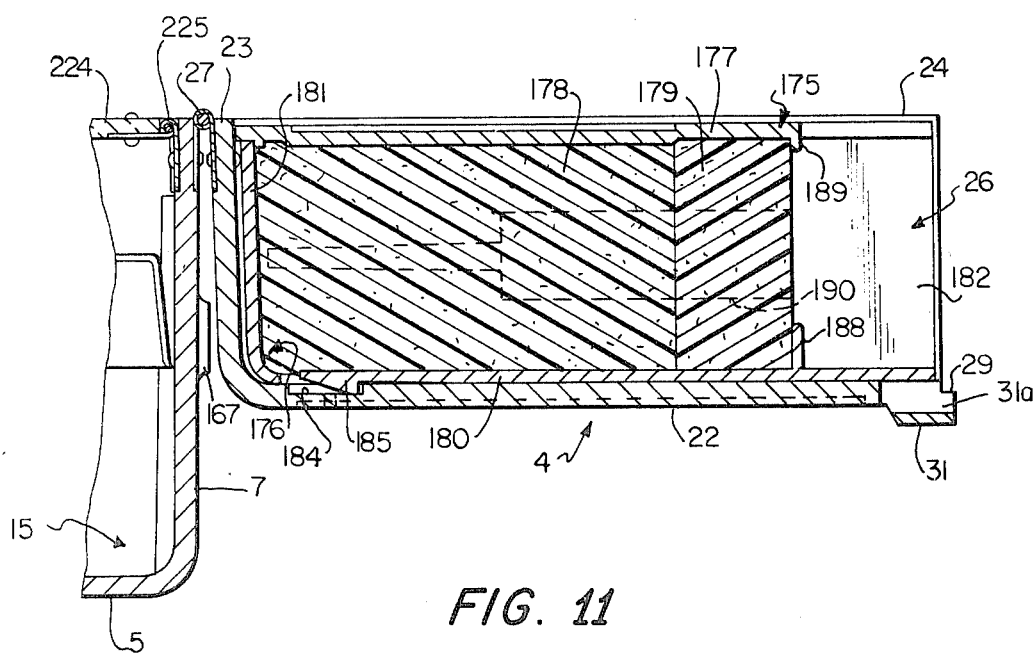
FIG. 11 is a transverse cross-sectional view taken generally on line 11—11, FIG. 10, on a larger scale than FIG. 10.

When housing portion 4 is in its fully open position, FIG. 11, side wall 23 is adjacent side wall 7 of housing portion 3. Two magnetic latches (not shown) identical to latches 165 are provided to secure housing portion 4 in its fully open position. In that position, cover 177 of unit 175 is approximately coplanar with flanges 56 and wall portions 58, 79, 80 of tray 53.

Turning again to FIGS. 16-19, vertical partition 40 has, on its side opposite ledge 50, two straight horizontally extending closely spaced retaining flanges 195 and a second pair of like flanges 196. In the space between the lower one of flanges 196 and lower flanged end 43, partition 40 has two straight vertically extending closely spaced flanges 197, 198. Nearer to free edge 49 of body 41 than is flange 198, flange 197 projects laterally from body 41 for a smaller distance than does flange 198, as best seen in FIG. 18. Free edge portion 49 has two integrally formed identical catch members 199, one located midway between partitions 195 and flanged end 42, the other midway between partitions 196 and flanged end 43. As best seen in FIG. 19, each catch member 199 is formed to provide a straight retaining groove 200 extending along the free frontal edge of partition 40 and, with the partition properly installed, opening toward side wall 7 of housing portion 2.

Along its lower half, side wall 7 of housing portion 2 is formed with a plurality of horizontally extending vertically spaced support bosses 201, FIG. 9, having front end faces 202 which are coplanar with the front face of flange 198. Midway of its length, side wall 7 has two pairs of closely spaced horizontal flanges 203, FIG. 9, one pair of flanges 203 being aligned horizontally with flanges 195 and the other pair with flanges 196 when partition 40 is in place. Two identical horizontal partitions 204 are provided, one inserted between and retained by flanges 195 and the corresponding pair of flanges 203, the other inserted between and retained by flanges 196 and the corresponding pair of flanges 203, as will be apparent from FIG. 8. Each partition 204 has a flat main body 205 having straight side edges 206 and 207, a straight rear edge 208 and a straight front edge 209 provided at its midpoint with an access notch 210. On one side, body 205 is provided with two integral, mutually parallel, closely spaced flanges 211, 212 which extend parallel to edge 208 and are spaced therefrom by a distance such that, when the partition is installed, the front face of flange 212 is coplanar with the front face of flange 198 and end faces 202 of bosses 201. The one of partitions 204 retained by flanges 196 is disposed with its flanges 211, 212 exposed downwardly. The other partition 204 is disposed with its flanges 211, 212 exposed upwardly.

An article support tray 215, FIGS. 5 and 9, is disposed in the space below the lowermost partition 204 and end wall 9. Thermoformed from thin transparent polymeric material, tray 215 has a front wall 216, side walls 217, 218 and end walls 219, the side and end walls being disposed rearwardly of the front wall and having outwardly flanged free edges. Free edge 217a of wall 217 is engaged between flanges 197, 198 of partition 40. Free edge 218a of wall 218 is engaged with front end faces 202 of bosses 201. The outwardly turned free edge of upper end wall 219 is engaged between flanges 211, 212 of the lower one of partitions 204. Front wall 216 is formed with depressions 220 each shaped to hold a laryngoscope 221, FIG. 5, and a depression 222 shaped to hold airways 223. A flat cover 224, FIG. 9, is mounted on side wall 7 of housing portion 2 by hinge 225, the cover 224 being of such plan shape and dimensions as to completely close that portion of storage space defined by lowermost partition 204 and the cooperating portions of partition 40 and walls 7, 9. Free edge 226 of cover 224 is provided with a flange 227 dimensioned to engage in groove 200 of the lower catch portion 199 of partition 40. So secured, the free edge portion of cover 224 rests on the free edge of partition 40 and the cover is held parallel to wall 5 and sufficiently near the front wall of tray 215 to maintain articles 221, 223 in place in the tray. Cover 224 is provided with a circular finger hole 224a, FIG. 5, and the cover is made adequately flexible to allow disengagement from catch member 199 when the cover is pulled forwardly by a finger inserted in hole 224a.

Figure 27:
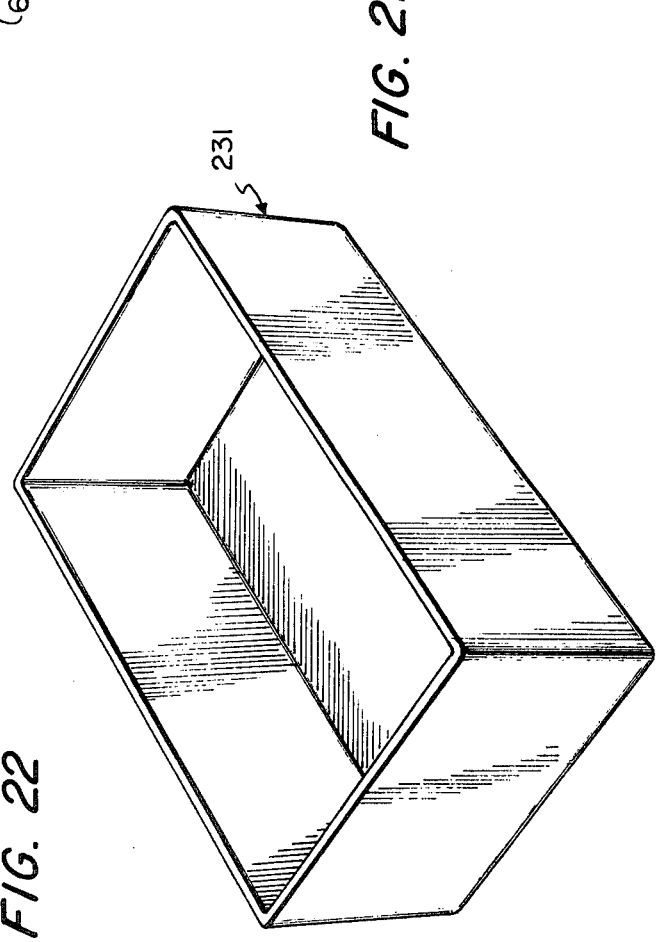
FIG. 27 is a perspective view of a tray employed in the main housing portion of the kit.

A second cover 228, FIG. 5, is mounted on side wall 7 by hinge 229. Cover 228 has a plan configuration and dimensions such as to cover all of the space between partition 40 and side wall 7 above cover 224 and its free edge 230 is provided with a flange to engage in the groove 200 of the upper one of catch members 199. When closed and secured by its catch member 199, cover 228 is coplanar with cover 224. A circular finger hole is provided at 228a. The space between partition 204 accommodates an open-top tray 231, FIG. 27, which is rectangular in plan, side and end elevation, has a flat bottom wall and straight top edges, and has a height only slightly smaller than the vertical space between partitions 204 so that, when tray 231 is in place as seen in FIGS. 5 and 8, miscellaneous articles retained in the tray cannot escape. The space between upper partition 204 and upper end wall 8 accommodates relatively bulky articles, e.g., a container of dextrose solution for intravenous administration.

As seen in FIG. 1, wall 16 of housing portion 3 and wall 22 of housing portion 4 are provided with shallow outwardly opening rectangular recesses 235, 236 and 237, 238, respectively, to provide areas on which indicia is displayed, as by being applied directly to the flat recessed surface 239, FIG. 15, or by being carried by a card adhesively secured to that surface. Thus, drug expiration information can be displayed in area 235, recommended cardiopulmonary resuscitation treatments and procedures can be summarized in area 236, the kit identification can be presented in area 237, and the contents of the kit can be listed in area 238. Main wall 118 of cover 102 for unit 100 can be similarly recessed in rectangular areas 239 and 240, FIG. 5, with the recommended cardiopulmonary resuscitation treatments and procedures being repeated in area 239 and an attendant's record pad being provided in area 240. Cover 177 for article retaining unit 175 can likewise be recessed in rectangular area 241, and the recommended dosages for medicines contained in housing portion 4 can be displayed in area 241.

Advantageously, a color coding system is employed for quick and certain identification of the medicines stored in injector vials 65, 66 and 88. In a typical form of the kit when employed for cardiopulmonary resuscitation, all three vials 65 are 50 ml. vials which contain adult doses of sodium bicarbonate solution, the stoppers 65a of the vials 65 are red, and the front face of tray wall 58 is red. The upper left one-quarter 89a of the front face of plate 89, as viewed in FIG. 5, is colored red, the two vials 88 extending therethrough contain pediatric doses of sodium bicarbonate solution, and the forwardly exposed end surfaces of the stoppers for those vials carry red discs 242. Rectangular portion 98b of the front face of plate 89 is colored light brown, the two vials extending through that portion contain atropine, and the stoppers for those two vials carry light brown discs 243. The full lower half 89c of the front face of plate 89 is colored pink, the four vials extending therethrough contain lidocaine, and the stoppers of those vials carry pink discs 244. The rectangular upper half 90a of the front face of plate 90 is colored dark brown, the four vials extending therethrough contain calcium chloride solution, and the stoppers for those vials carry dark brown discs 245. The lower half 90b of the front face of plate 90 is colored dark blue, the four vials extending therethrough contain epinephrine and the stoppers for those vials carry dark blue discs 246. The upper left quarter 91a of plate 91 is colored dark brown, the two vials extending therethrough contain aminophylline, and the stoppers for those vials carry dark brown discs 24. The upper right quarter 91b of the front face of plate 91 is colored light blue, the vials extending therethrough contain dexedrine and the stoppers for those vials carry light blue discs 248. The lower left quarter 91c of the front face of plate 91 is colored yellow, the two vials extending therethrough contain ephedrine and the stoppers for those vials carry yellow discs 249. The lower right quarter 91d of plate 91 is colored green, the two vials extending therethrough contain diphenhydramine and the stoppers for those vials carry green discs 250. Thus, al of the injector vials 65 and all of the injector vials 88 above vial 66 contain specific medicines useful in cardiopulmonary resuscitation, and each vial is color coded to identify the particular medicine it contains.

The vials below those just described contain medicines useful for anaphylaxis resuscitation and these vials are also color coded for ease of quick identification. The front faces of wall portions 79, 80 of tray 53 are colored purple, vial 66 contains dextrose solution, and the stopper for that vial is of matching color. The square area 92a of the front face of plate 92 is colored rose, the vial passing therethrough contains metaraminol bitartrate solution, and the stopper of that vial carries a rose colored disc 251. The adjacent square area 92b is colored salmon, the vial extending therethrough contains lidocaine at 20%, and the stopper for that vial carries a salmon colored disc 252.

What is claimed is:

1. In a portable kit for use in medical emergencies, the combination of a main upright housing portion defining a first storage space which opens forwardly;

secondary housing means which defines at least a second storage space;

mounting means mounting at least a portion of said secondary housing means on said main housing portion for movement between a closed position, in which said second storage space opens toward said first storage space, and an open position, in which said second storage space is disposed beside said first storage space and opens forwardly;

first article-retaining means disposed in a predetermined location and orientation in said first storage space and comprising first support means defining a plurality of forwardly opening recesses each dimensioned to receive and support a medicine injector vial, and plate means disposed in upright position in front of said first support means and including a plurality of apertures each aligned with a different one of said recesses;

second article-retaining means disposed in a predetermined location and orientation in said second storage space and comprising second support means defining a plurality of recesses which extend across said second storage space and open away from said main housing portion when said portion of said secondary housing means is in said open position, each of said recesses of said second support means being dimensioned to accommodate a syringe unit with a portion of the syringe unit exposed to view when said portion of said secondary housing means is in said open position, each of said recesses of said second support means being aligned horizontally with at least one of the forwardly opening recesses of said first support means, said at least one forwardly opening recess being dimensioned to accommodate and support a medicine injector vial of the size to be employed with the syringe unit accommodated by the recess of said second support means with which it is horizontally aligned, whereby the user of the kit, having chosen a medicine injector vial from said first article retaining means, can quickly select the related syringe unit from said second article retaining means without need for inspection of the syringe unit to assure that the proper syringe unit has been selected.

2. The combination defined in claim 1, wherein said main housing portion comprises
a rear wall,
two side walls joined to said rear wall and projecting forwardly therefrom, at least one of said side walls having a flat frontal edge portion,
upper and lower end walls joined to said rear wall and projecting forwardly therefrom,
said lower end wall being flat and of an area adequate to serve as a base for supporting the kit in its upright position,
said rear, side and end walls cooperating to define said first storage space;
said secondary housing means comprises
a main wall,
a side wall extending along and joined to one edge of said main wall, said side wall projecting from said main wall and having a flat free edge portion, and
upper and lower end walls joined to said main and side walls,
said main, side and end walls cooperating to define said second storage space;
said means mounting said secondary housing means on said main housing portion comprises a hinge secured to said flat frontal edge portion of said one side wall of said main housing portion and to said flat free edge portion of said side wall of said secondary housing means;
said main wall of said secondary housing means has a flat free edge portion opposite said side wall, and said second storage space also opens away from said side wall; and
said second article-retaining means is in the form of a removable unit.

3. The combination defined in claim 2, wherein said removable unit comprises
a shell having a main wall, a side wall and upper and lower end walls, said shell being of a configuration and having dimensions such as to be capable of being inserted into said second storage space from the open side thereof until the side wall of the shell is in flush engagement with the side wall of the secondary housing means, the main wall and upper and lower walls of the shell then being in flush engagement with the corresponding walls of the secondary housing means, a cover engaging the free edges of the walls of said shell, the free edge of said cover being parallel to and spaced from the free edge of the main wall of said secondary housing means toward said side walls, and at least one body of foamed polymeric material disposed within and substantially filling the space defined by said shell and said cover and having a face which is directed away from said side walls and toward said flat free edge portion of the main wall of the secondary housing means,
said recesses of said second support means being bores in said at least one body of foamed polymeric material and opening through said face.

4. The combination defined in claim 3 and further comprising
latch means operative, when said side walls are in mutual engagement, to restrain said shell against movement away from the side wall of the secondary housing means, said latch means comprising
a fixed latch member carried by one of said main walls, and
a resiliently movable latch member carried by the other of said main walls.

5. In a portable kit for use in medical emergencies, the combination of
a main upright housing portion comprising
a rear wall,
two side walls joined to said rear wall and projecting forwardly therefrom, at least one of said side walls having a flat frontal edge portion,
upper and lower end walls joined to said rear wall and projecting forwardly therefrom,
said lower end wall being flat and of an area adequate to serve as a base for supporting the kit in its upright position,
said rear, side and end walls cooperating to define a first storage space which opens forwardly;
secondary housing means comprising
a main wall,
a side wall extending along and joined to one edge of said main wall, said side wall projecting from said main wall and having a flat free edge portion, and
upper and lower end walls joined to said main and side walls,
said main, side and end walls cooperating to define a second storage space;
mounting means comprising a hinge secured to said flat frontal edge portion of said one side wall of said main housing portion and to said flat free edge portion of said side wall of said secondary housing means, said mounting means supporting said main, side and end walls for movement between a closed position, in which said second storage space opens toward said first storage space, and an open position, in which said second storage space is disposed beside said first storage space and opens forwardly;
first article-retaining means disposed in a predetermined location and orientation in said first storage space and comprising a plurality of article retainers each occupying a different predetermined position which is observable from in front of the kit when the kit is upright and said secondary housing means is open, said first article-retaining means comprising
at least one body of foamed polymeric material having a plurality of forwardly opening article-retaining bores, and
tray means supported by said main housing portion and extending across said at least one body of foam material, portions of said tray means defining article-accommodating openings each registered with a different one of said bores;
second article-retaining means disposed in a predetermined location and orientation in said second storage space and comprising a second plurality of article retainers each occupying a predetermined location on said second article-retaining means,
each of said predetermined locations on said second article-retaining means being aligned horizontally with at least one of said predetermined positions on said first article-retaining means when said secondary housing means is in said open position,
whereby the user of the kit, having chosen an article from said first article-retaining means, can quickly select a related article from said second article-retaining means without need for inspection of the related article to assure that the related article has been correctly selected.

6. The combination defined in claim 5, wherein
said tray means comprises vertical side walls and a plurality of vertically spaced horizontal partitions extending between said vertical side walls to define a plurality of rectangular openings equipped with coplanar locator flanges; and
said portions of said tray means defining said article-accommodating openings are rectangular plates each disposed in a different one of said rectangular openings and engaging said locator flanges.

7. The combination defined in claim 5 and further comprising
a vertically extending partition disposed in said main housing portion and dividing said first storage space into left and right portions are viewed from the front of the kit,
said first article-retaining means being disposed in said left portion;
the combination further comprising
transparent cover means hinged to the other of said side walls of said main housing portion,
the width of said cover means being such that the cover means engages said partition when the cover means is closed; and
coacting latch elements carried respectively by said cover means and said partition to secure the cover means when closed.

8. The combination defined in claim 7, wherein
said secondary housing means further comprises a second housing portion defining a third storage space,
the combination further comprising
a second hinge interconnecting said second housing portion of said secondary housing means and the other side of said main housing portion and thereby mounting said second housing portion for movement between a closed position, in which said third storage space opens toward said first storage space and said second housing portion extends over said transparent cover means, and an open position, in which said third storage space is disposed beside said first storage space and opens forwardly,
said first and second housing portions of said secondary housing means coacting to completely close the front of said first storage space when said first and second housing portions are in said closed positions.

* * * * *